United States Patent [19]

Slivenko et al.

[11] 4,108,173

[45] Aug. 22, 1978

[54] BLOOD ACCESS DEVICE

[75] Inventors: Victor Slivenko, San Diego; Michael R. Emken, Encinitas, both of Calif.

[73] Assignee: General Atomic Company, San Diego, Calif.

[21] Appl. No.: 786,499

[22] Filed: Apr. 11, 1977

[51] Int. Cl.² ............................................ A61M 5/00
[52] U.S. Cl. ................................. 128/214 R; 128/348
[58] Field of Search ............... 128/1 R, 214 R, 214 B, 128/348, 350 R, 334 R, 274

[56] References Cited

U.S. PATENT DOCUMENTS

| | | | |
|---|---|---|---|
| 2,935,068 | 5/1960 | Donaldson | 128/348 |
| 3,505,991 | 4/1970 | Hellerstein et al. | 128/1.1 |
| 3,663,965 | 5/1972 | Lee et al. | 128/348 X |
| 3,765,032 | 10/1973 | Palma | 128/348 X |
| 3,783,868 | 1/1974 | Bokros | 128/348 X |
| 3,815,577 | 6/1974 | Bucalo | 128/1 R |
| 3,998,222 | 12/1976 | Shihata | 128/214 R |
| 4,015,601 | 4/1977 | Bokros et al. | 128/214 R |

Primary Examiner—Dalton L. Truluck
Attorney, Agent, or Firm—Fitch, Even, Tabin & Luedeka

[57] ABSTRACT

A device to provide access to the circulatory system of a living body for simultaneous withdrawal and return of blood to the system includes a tubular conduit and a housing integrally associated with the conduit and having fluid communication therewith through at least one aperture in the conduit wall located at the point where the conduit adjoins the housing. The relation between the housing and the conduit is such that the axes of both intersect at right angles. The housing extends the fluid communication to a point outside the living body. Inside the housing is a movable valve body which has a pair of ports alignable with the aperture. The valve body is movable in the housing between positions of alignment and nonalignment of the apertures and the port to selectively establish fluid communication between the circulatory system and the outside of the living body.

9 Claims, 12 Drawing Figures

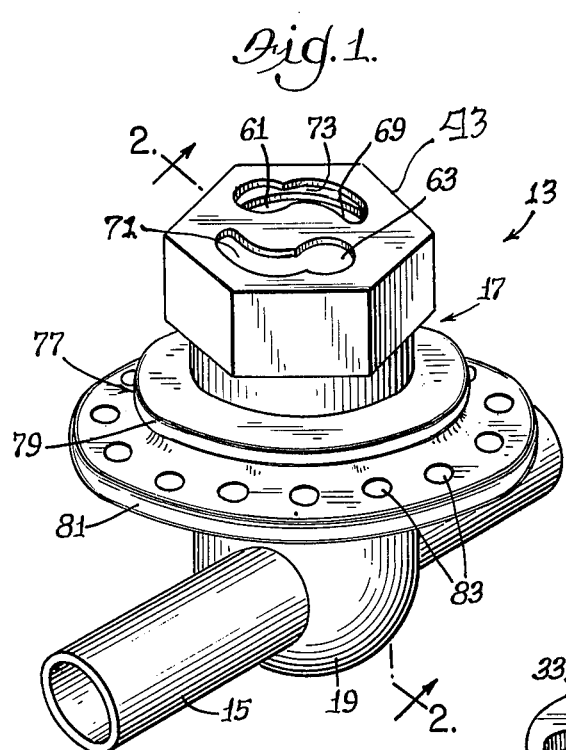
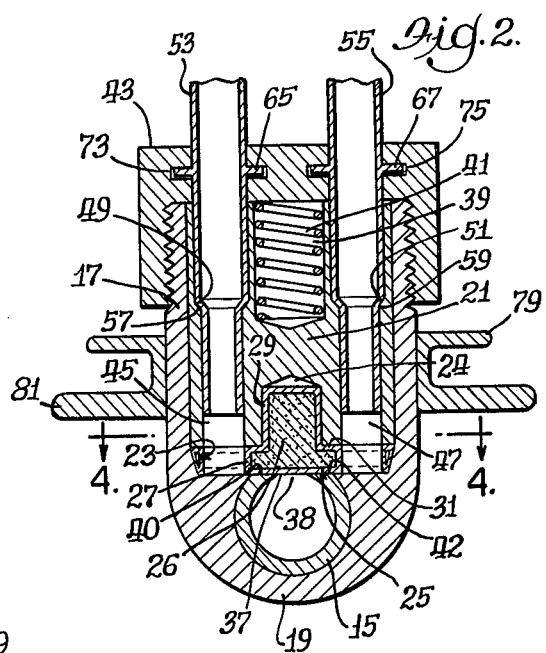
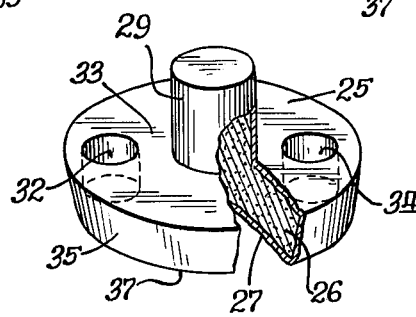
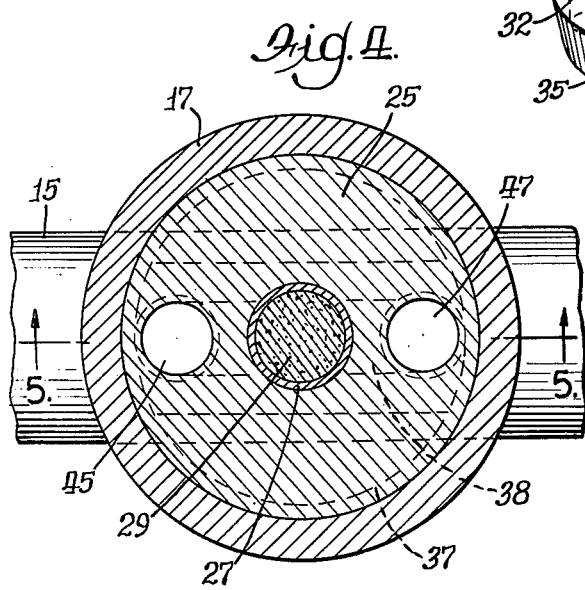
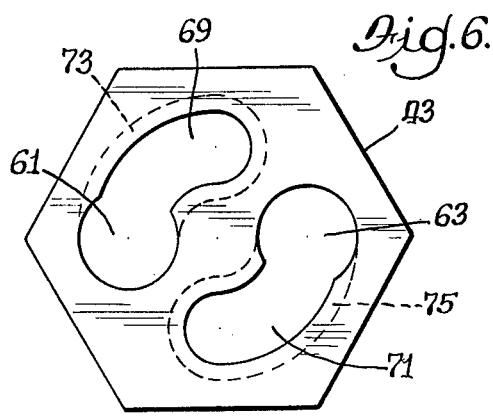
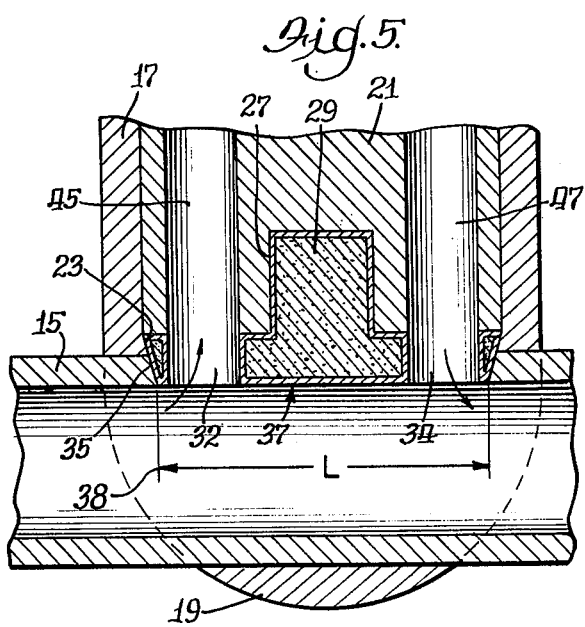

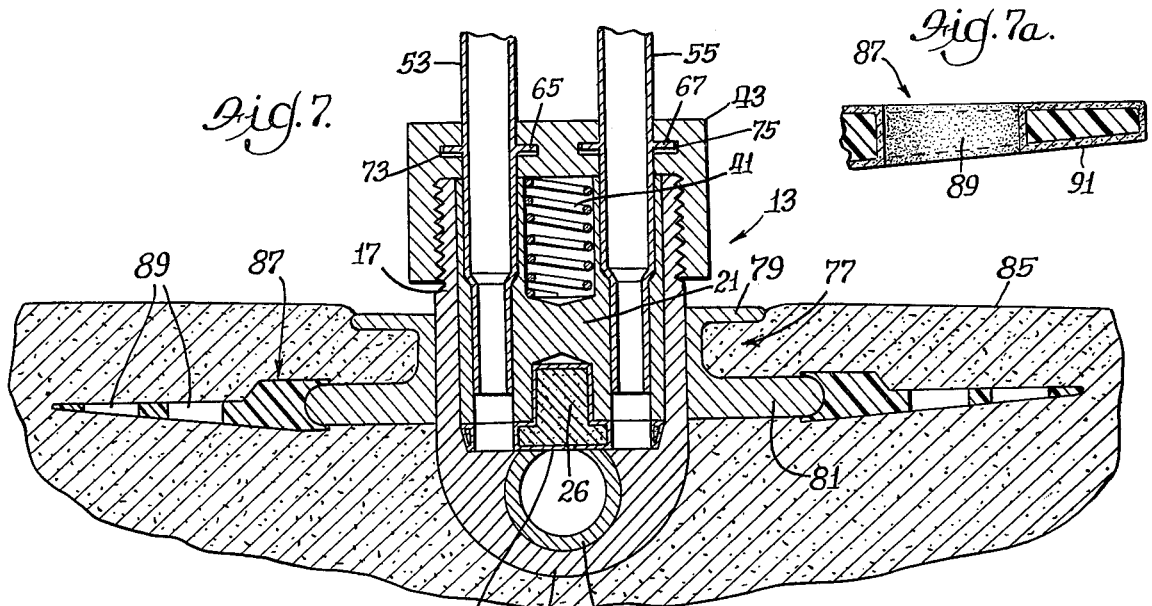
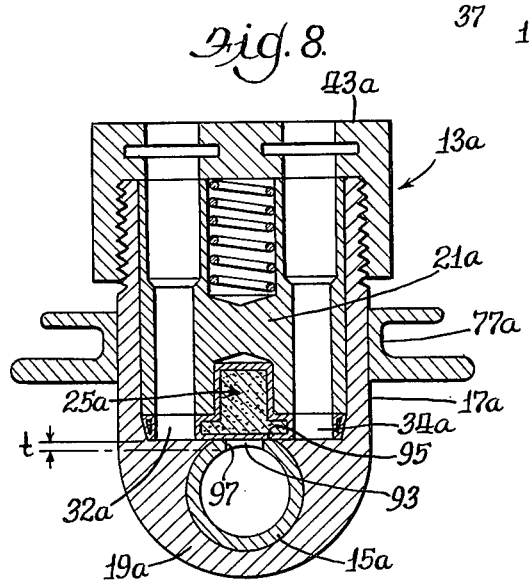
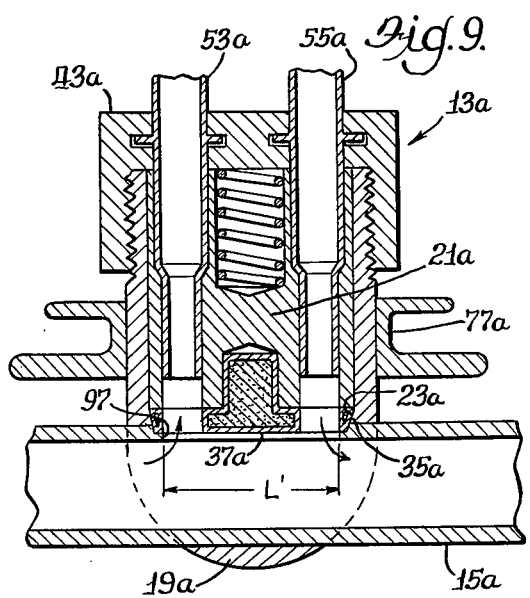
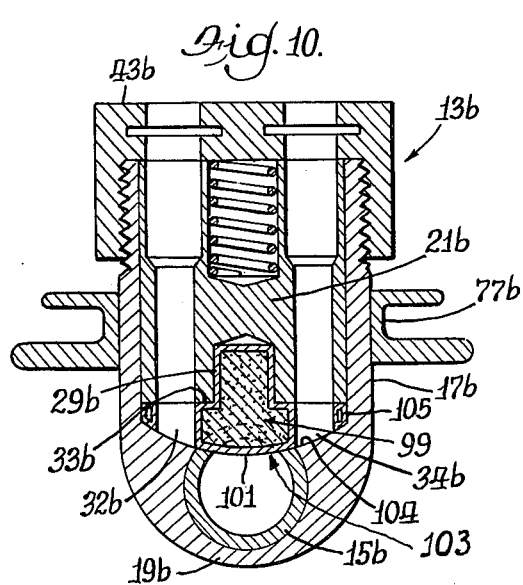
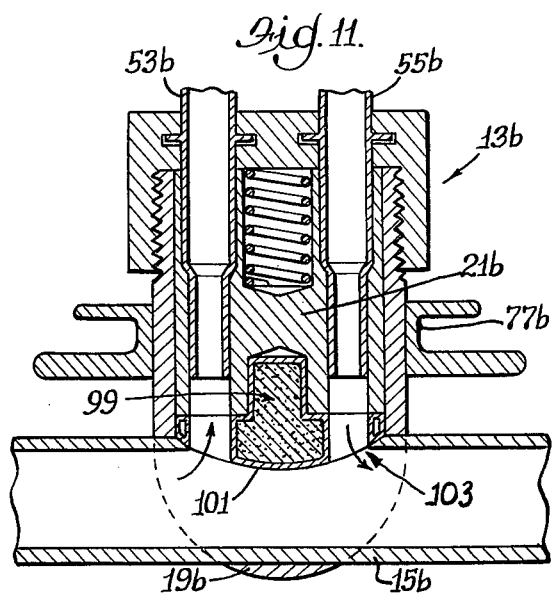

BLOOD ACCESS DEVICE

This invention relates to medical devices and, more particularly, to a device to provide access to the circulatory system of a living body for simultaneous withdrawal and return of blood to the circulatory system.

There is a need for a device to provide access to the circulatory system of a living body in circumstances requiring, for example, simultaneous withdrawal from and return of blood to the circulatory system while passing the blood externally through a blood dialyzer. An individual could require this over an extended period of time, and it is desirable for a device in the form of an implant to be available in the body for immediate connection of catheters to the circulatory system at any desired time. As an implant, however, such a device should be biologically compatible with the living tissues surrounding it. In this connection, the device should not prevent healing, irritate tissues, or stimulate a prolonged rejection response by the living body. Further, the device should be physiologically inert over prolonged periods of time and should be mechanically strong and reliable.

In copending application Ser. No. 622,090, filed Oct. 14, 1975, now U.S. Pat. No. 4,015,601 issued Apr. 5, 1977, and assigned to the assignee of this invention, an access device is described which provides means for forming fluid communication between the outside and the circulatory system with fluid passage in one direction at a time. In copending application Ser. No. 764,207, filed Jan. 31, 1977, and also assigned to the assignee of this invention, an access device is described which provides for simultaneous withdrawal from and return of blood to the circulatory system. The invention of that application proceeds on the basis that withdrawal and return of blood with respect to the circulatory system are respectively from two separated points in the system. Accordingly, two separate tubes are provided, one for insertion longitudinally in a blood vessel and the other for connection to a bypass in the form of a graft either upstream or downstream of the same blood vessel.

Like the access device of copending application Ser. No. 764,207, the access device of this invention provides for simultaneous withdrawal from and return of blood to the circulatory system. At the same time, this is accomplished in a device that is structurally simple and has desirable liquid and bacterial seals with relatively little pyrolytic carbon used both to form the seals and to coat the surfaces in contact with blood.

Accordingly, it is a primary object of this invention to provide an improved device for insertion into a blood vessel of the circulatory system that will afford access to the blood stream for simultaneous withdrawal and return of the blood.

It is another object of this invention to provide a device of the aforementioned type that has a single tube for insertion in the circulatory system of a living body.

The accomplishment of these and other objects of the invention will become apparent from the following description and its accompanying drawings of which:

FIG. 1 is a perspective view of a blood access device embodying various features of the invention and adapted for implantation in a living body;

FIG. 2 is a vertical sectional view of the device of FIG. 1 taken along the line 2—2 and illustrating inserted catheters but with parts nonaligned (valve closed) to prevent fluid passage through the catheters;

FIG. 3 is a perspective view of a tip insert used in the device of FIG. 2 with a cut away portion to illustrate the inside structure;

FIG. 4 is a horizontal sectional view of the device of FIG. 2 taken along the line 4—4 but illustrating parts aligned (valve open) for fluid passage;

FIG. 5 is a fragmentary vertical sectional view taken along the line 5—5 of FIG. 4 and also illustrating parts aligned for fluid passage;

FIG. 6 is a top view of the cover of the device of FIG. 1;

FIG. 7 is a view similar to FIG. 2 and showing the device in the environment of a living body and including a ring flange to enhance the implantation of the device;

FIG. 7a is an enlarged view of a portion of the ring flange illustrating a coating on all surfaces;

FIG. 8 is a vertical sectional view similar to FIG. 2 but showing an alternative form of the device;

FIG. 9 is a vertical sectional view taken longitudinally of the alternative form of the device of FIG. 8;

FIG. 10 is a vertical sectional view similar to FIG. 2 but showing another alternative form of the device; and FIG. 11 is a vertical sectional view taken longitudinally of the alternative form of the device of FIG. 10.

The device of the invention includes two principal outer portions which are generally at right angles to one another. One portion is a tube having open ends for insertion longitudinally in a blood vessel. The other major portion is a housing with one end open and the other closed, the housing containing a valve for establishing fluid communication between the inside of the device and the blood in the blood vessel. The valve is adapted to receive a twin-conductor catheter which is used to establish a blood flow line simultaneously in and out of the circulatory system. The device is structured of materials that are biologically compatible with the blood and the tissues of the living body in which it is inserted. At least all blood contacting surfaces are carbon. Further, the materials are physiologically inert over prolonged periods of time and provide a device that is mechanically strong and reliable, all of which is described in detail hereinafter.

Referring now to FIG. 1, there is shown a blood access device 13 having a conduit 15 and a housing 17 having a closed end 19, the conduit being adjoined at the closed end. In this illustrated embodiment, the conduit 15 is a round tubular open-ended structure, and the housing 17 is generally cylindrical in form. The conduit 15 is generally at right angles to the axis of the housing 17, and, as fully described hereinafter, the conduit is related to the housing such that the axes of the two intersect each other. Further, such intersection is at right angles.

In FIG. 2 will be seen a valve body 21 that is mounted internally of the housing 17. It will be noted that the housing 17 is generally cylindrical both on its outer and inner portions, except for a lower inner portion 23 which is tapered inwardly at the closed end of the housing. The valve body 21 is generally cylindrical and preferably is machined from metal, such as titanium. A bore 24 is provided in the inner end of the valve body 21 to receive a tip insert 25, shown separately in FIG. 3. The tip insert 25 structure includes a graphite core 26, the outer surfaces of which are covered with a pyrolytic carbon coating 27. The insert 25 includes an integral mounting stem 29 which is sized to fit snugly in the bore 24 in the inner end of the valve body. The inner end of the valve body 21 has a surface 31 which is machined or faced to provide a flat mounting surface for a mating top face 33 of the tip insert 25. A pair of holes 32 and 34 are provided through the body of the tip insert 25. These holes are located on a diameter of the insert and are spaced apart 180° on either side of the mounting stem 29. The purpose of these holes is to establish fluid communication through the tip. This communication is described more fully hereinafter. The tip insert is mounted in the end of the valve body and affixed in this mounted position by a suitable epoxy or cement. This provides a pyrolytic carbon tip for the valve body which is important for forming a proper fluid and bacterial seal more fully described hereinafter. In this connection, however, the tip insert 25 includes a circumferential surface 35 which tapers inwardly and away from the top surface 33 to a bottom face 37. The width of the circumferential surface 35 and its taper are provided to closely conform to the tapered inner portion 23 of the housing. The interface thus formed between these tapered surfaces along with the pyrolytic carbon face 37 are important features in forming the seal in accordance with the invention.

The conduit 15 is provided with an aperture in the form of a slot 38 that extends under the face 37 of the valve. The conduit is located in the closed end of the housing 17 such that the wall of the conduit would intersect the interior of the housing if it were continued. This portion of the conduit wall, however, is lapped to flatten a portion of the tubular wall. The lapping is continued to a depth sufficient to generate the slot 38 in the wall of the conduit 15 to a width substantially equal to the diameter of the holes 32 and 34 in the tip insert 25. Preferably, the conduit 15 is made of pyrolytic carbon as described in detail hereinafter, and the lapping causes flat side surfaces 40 and 42. These side surfaces, along with the bottom face 37 of the valve that preferably also is lapped and polished flat, are effective in forming a liquid and bacterial seal on the side of the slot, where the valve is either closed or open, as described hereinafter.

In FIGS. 4 and 5 it will be seen that the slot 38 is of length "L" and is equal in length of the diameter of the bottom face 37. The ends of the slot 38 are curved accordingly, and the liquid and bacterial seal is effected at these ends between the pyrolytic carbon circumferential surface 35 of the tip insert 25 and the combined adjacent tapered surface of the conduit 15 wall and the tapered inner portion 23 of the housing (FIG. 5).

The valve body 21 is coaxially rotatable within the housing 17. It is important that the valve body 21 form a tight seal with the interior of the housing when in a proper seated relation and that this seal be retained during rotation of the valve body as well as when the valve body is at rest. For this purpose, a bore 39 is provided in the center of the outer end of the valve body 21 to contain a compression means, such as a suitable coil spring 41. A cap 43 is applied over the open end of the housing 17 and the valve body 21, including the compression means or coil spring 41. The cap 43 is of a screw type, and the outer surface of the housing 17 near its open end is threaded to accommodate the cap 43. The inner top surface of the cap 43 bears down upon the spring 41 to place the spring in a compressed condition in the bore 39 to securely retain the valve body 21 in a seated condition within the housing 17.

The valve body 21 has a pair of generally cylindrical longitudinal passages 45 and 47 spaced apart 180° from each other along a diameter of the valve body 21 and on either side of the bore 39. These passages are generally parallel to one another. The diameter of each of the passages 45 and 47 decreases at a point approximately halfway through the valve body at beveled surfaces 49 and 51 respectively. Apart from these beveled surfaces, the diameters of both the longitudinal passages are constant, albeit the diameter of the passages at one end of the bevel is smaller than the diameter of the passages at the other end.

It was mentioned earlier that the tip insert 25 is affixed in a suitable manner in the inner end of the valve body 21. It will now be understood that the location and size of the holes 32 and 34 in the insert and the longitudinal passages 45 and 47 are predetermined to match and that the insert is located before affixing so that the holes 32 and 34 are aligned with the longitudinal passages to establish the needed fluid communication through the valve when the valve is rotated to the open position. In this connection, FIG. 2 shows the device with the valve body 21 closed, i.e., rotated such that the passageways 45 and 47 are not aligned with the slot 38. Thus, there is no fluid communication between the interior of the conduit 15 and the passages and no blood will flow therethrough. FIGS. 4 and 5, on the other hand, show the valve open, i.e., rotated so that the passages 45 and 47 are aligned with the slot 38 to establish blood flow.

These longitudinal passages 45 and 47 receive catheter tips 53 and 55 respectively to complete a flow path for the blood when a blood passage is established. These catheter tips have diameter portions that conform very closely to the inner diameters of the longitudinal passages so as to form a close-fitting relation therewith. The catheter tips include beveled surfaces 57 and 59 respectively at the points where their outer diameters decrease. These beveled surfaces conform very closely to the size and angle of the beveled surfaces 49 and 51 respectively in the longitudinal passages so as to form a seal at the interface between opposing surfaces when the catheter tips are inserted and seated in their respective longitudinal passages.

The seated condition of the inserted catheter tips occurs through an interlocking means established between the cap 43 and the catheter tips 53 and 55. As best seen in FIG. 6, the cap 43 is provided with a pair of generally circular orifices 61 and 63 spaced apart from each other 180° along a diameter of the cap 43. Such spacing corresponds to the location of the longitudinal passages in the valve body 21 so that when the cap 43 is in place, the orifices 61 and 63 will open directly into the longitudinal passages 45 and 47 respectively when the valve body is rotated to the aligned condition. The catheter tips 53 and 55 are provided with lugs 65 and 67 respectively extending outwardly at right angles from their respective catheter tip walls. These lugs may take the form of a complete ring around the tips, a semi-circular arrangement around the tips, or a split arrangement extending oppositely from the walls along a diameter of the tips. The orifices 61 and 63 are large enough to receive not only the catheter tips, but also the lugs 65 and 67 respectively.

It would be completely undesirable for the catheters to be removable when the valve is open and blood is flowing. To avoid such a circumstance, an interlock system is provided to lock the catheters in place when the valve is open and to permit removal of the catheters only when the valve is closed. This is accomplished in accordance with the invention by a pair of opposing curvilinear slots 69 and 71 extending peripherally in the same direction from one side of the orifices 61 and 63 respectively. The arc of each is approximately one-quarter of a circle. The slots 69 and 71 are wide enough to allow passage therethrough of the catheter tips 53 and 55 respectively, but will not pass the lugs 65 and 67. An inner locking slot 73 is provided in the body of the cap 43 under its top surface to inwardly extend the perimeter of the slot 69 in its arcuate direction in the body only of the cap to a width equal to the orifice 61. In similar fashion, an inner locking slot 75 is provided in connection with the arcuate slot 71, all as indicated. Thus, the slots 73 and 75 permit the passage of the lugs 65 and 67 therethrough while the slots 69 and 71 permit the passage of the catheters 53 and 55 respectively therethrough. As viewed in the illustrated embodiment, the catheter tips 53 and 55 may be used as handles to rotate the valve body 21 within the limits of the arcuate slots 69 and 71, which represents a 90° rotation from an initial position of alignment of the longitudinal passageways 45 and 47 with the apertures 61 and 63 respectively. After such rotation, the valve is open and a passage for blood is established as indicated in FIG. 5. The blood may flow outwardly from the conduit 15 and inwardly to the conduit 15 simultaneously as indicated by the direction of the flow arrows.

To interrupt the blood passage, the valve body 21 is rotated in a reversed direction one-quarter of a turn so that the passageways 45 and 47 are nonaligned with the slot 38 in the conduit 15 (the condition shown in FIG. 2).

Thus, a seal means for the device 13 is provided and a liquid and bacterial seal is maintained between the pyrolytic carbon bottom face 37 of the tip insert 25 and the surfaces 40 and 42 of the slot 38 (FIG. 2) at the sides of the slot 38 and between the interfaces of the opposing tapered surfaces 33 and 35 of the wall of the conduit 15 at the ends of the slot 38 (FIG. 5).

Although the arrows in FIG. 5 indicate a directional flow from the interior of the conduit 15 outwardly through the longitudinal passage 45 and return through the longitudinal passage 47 to the interior of the conduit 15, it should be understood that this is for the purpose of depicting a simultaneous outward and return flow of a fluid in the blood access device 13, rather than for stressing a particular direction of flow. The direction of both arrows could be reversed to indicate a reversed direction of flow in accordance with the invention.

It has already been mentioned that the catheter tips 53 and 55 are used as instruments to rotate the valve body 21 to align the longitudinal passages with the slot 38 in the conduit 15. The catheter tips, of course, are inserted into the longitudinal passages when the valve is closed, i.e., when the longitudinal passages 45 and 47 are in a nonaligned relation with the slot 38. The catheter tips do not need to extend the full length of the longitudinal passages, and it will be noted in FIG. 2 that the inner ends of the catheter tips 53 and 55 terminate short of the bottom of their respective longitudinal passages. The close-fitting relation along the entire outer surfaces of the catheter tips when inserted in the passageways is effective in providing the liquid and bacterial seal between these parts. It is important, however, that the interfacing bevel surfaces 49-57 and 51-59 are lapped and polished to form good seats to assure proper seals. Accordingly, it is important to carefully determine the distances between the interfacing beveled surfaces and the lugs 65 and 67 and their corresponding slots 73 and 75 respectively to maintain these seats once they are established. The bacterial seal is a barrier to the invasion of bacteria in the blood stream through the interfaces of these parts of the blood access device 13.

The catheter tips 53 and 55 are at the ends of catheter tubes (not shown) which may be, at the discretion of the user, either two completely separate flexible tubes or breakouts from a single dual-conductor type catheter, such as one having two side-by-side conduits therein or one having two concentric conduits.

Returning to FIG. 1, around the perimeter of the housing 17 is a stabilizing button 77 that has the appearance in a sectional view (e.g., FIG. 2) of a collar button, a smaller flange 79 being at one end of the button and a larger flange 81 being at the other end. In practice, this button is applied over the housing such that the smaller flange 79 will be disposed at the approximate level of the skin surface. These flanges on the button project outwardly from the housing, and the larger flange 81 carries a plurality of holes 83. When the blood access device 13 is implanted in a living body, body tissue will grow in and around the holes 83 and stabilize the position of the blood access device in the body. The position of the button 77 may be movable axially of the housing to control the extent the housing extends beyond the surface of the skin, or the position of the button may be fixed if uniformity of housing height above the flange is found to be desirable. Further, it may be desirable to also include an epithelium stopping means in the form of another collar (not shown) between the flanges 79 and 81, as described in U.S. Pat. No. 3,783,868, issued Jan. 8, 1974, to inhibit the progressive growth of epithelium tissue down and around the housing 17.

In FIG. 7, the device 13 is illustrated as implanted in a living body where the conduit 15 could be inserted in a blood vessel, such as an artery (not shown). It should be recognized that although the blood access device 13 is useful in a living human body, it may also have veterinary or scientific applications in other living animals, domestic or wild. Further, although its suggested use is in connection with an artery, it should be understood that this is for descriptive purposes only and that the device of the invention may be inserted in any part of a circulatory system as needed, and there is no intention of limiting its use to an artery.

The device 13 is inserted in the living body by any suitable surgical procedure. Generally, a longitudinal incision is made through the skin at the desired location for insertion in the blood vessel, and the blood vessel is severed after momentarily stopping the flow of the blood therethrough. The severed ends of the blood vessel are slipped over the protruding ends of the conduit 15. Sutures (not shown) are then used to sew up the skin around the housing 17 as illustrated. In this connection, it is noted that the length of the housing 17 above the point of association with the conduit 15 is sufficient to effectively extend from the blood vessel in which the conduit 15 is inserted to a point outside the living body, i.e., outside the skin layer 85.

To enhance particularly a rotative stabilized position of the device 13 in the human body, a flexible flange 87 is provided that attaches over the circumference of the larger flange 81 of the button 77. It, also, has a plurality of holes 89 through its surface. Body tissue will grow in and around these holes 89 and stabilize particularly the rotative position of the blood access device 13. The flange 87, preferably is of polypropylene and is more flexible than the flange 81 on which it is mounted. Thus, it affords a larger diameter for securing the rotative position without the larger diameter being rigid and possibly adversely affecting the insertion in the blood vessel.

As shown in FIG. 7a, all surfaces of the flexible flange 87 are covered with a thin coating 91 of carbon as described in detail hereinafter.

An alternative construction of the device 13 is shown in FIGS. 8 and 9 as device 13a. The difference in construction of the device 13a over the device 13 is in the seal means, i.e., in the relationship between the valve body 21 and the conduit 15. Only this difference in construction will be described in connection with the device 13a, it being understood that the rest of the construction is the same as that described for the device 13. The reference numbers for like parts carry the subscript "a".

In constructing the device 13a, the lapping of one side of the conduit 15a does not extend to a depth that cuts completely through the wall to form the aperture or slot 38 as in the device 13 (FIGS. 2 and 5). Rather, an aperture in the form of a slot 93 is provided in the wall of the conduit 15a by lapping the wall to a depth that provides a flat surface 95 on the outside of the conduit 15a while leaving an uncut thickness "t" (FIG. 8) in the conduit wall. A round-ended slot 93 is then cut through the longitudinal center of the remaining portion of the wall represented by the thickness "t", such as by routing or other suitable machining operation. As seen in FIG. 9, the slot 93 thus formed is shorter than the full diameter of the bottom face 37a of the valve. Thus, L' (FIG. 9) is shorter than L (FIG. 5). Accordingly, a portion of the flat surface of the bottom face 37a on the inside end of the valve body 21 always covers the entire slot, whether the valve is in the open position or in the closed position. This adds a flat interfacial portion between the bottom face 37 and the wall of the conduit 15a to the seal established also at the interface between the tapered inner portion 23a of the housing and the circumferential surface 35a in forming the liquid and bacterial seal of the device 13a. In this construction, the location of the rounded ends of the slot 93 is determined to coincide with the location of the outer portions of the circumferences of the holes 32a and 34a in the tip insert 25a. As mentioned in connection with the description of the device 13, the width of the slot 93 is substantially equal to the diameter of these holes 32a and 34a. A very narrow rim or blunt perimeter 97 defines the slot 93 in the wall of the conduit 15a. This blunt perimeter does not cause accumulation and coagulation of blood around the slot when the valve is closed, and it is believed that the reason for this is the general openness of the sides of the slot vis-a-vis the relative closed condition of the sides of small holes along with its orientation longitudinally with respect to the flow of blood in the blood vessel keep this area well flushed when the valve is closed. Thus, the primary difference in construction between the devices 13 and 13a (FIGS. 2 and 8 respectively) may be summarized by considering planes that parallel the axes of the respective conduits 15 and 15a and pass through the conduit walls. In the instance of device 13 (FIG. 2), the plane is such distance from the axis that it passes through the wall at a depth that exceeds the wall thickness and establishes an aperture in the form of a slot defined by the cut sides of the conduit wall, the length of the slot being established by the diameter of the bottom face 37. In the instance of the device 13a (FIG. 8), the plane is farther away from the axis and passes through the conduit wall at a depth that is less than the wall thickness and thereby establishes a flat through which the aperture is formed, as by routing. The length of the aperture is less than the diameter of the bottom face 37a.

Another alternative construction of the device 13 is shown in FIGS. 10 and 11 as device 13b. Again, the differences in construction here are in relation to the seal means, i.e., generally the inner end of the valve body 21 with respect to the conduit 15. Only the differences in construction will be described, it being understood that the rest of the structure is the same as that of the device 13. Reference numbers of like parts in this device carry the subscripts "b".

In this device, a tip insert 99 is affixed in the inner end of the valve body 21b in a manner similar to that described in connection with the tip insert 25 (FIG. 3) of the device 13. The tip insert 99 is the same as the tip insert 25 in all respects except for the bottom face. Whereas in the tip insert 25, the bottom face 37 is flat and generally parallel to the top face 33, a spherically shaped bottom face 101 is provided on the tip insert 99. The conduit 15b is then lapped with a matching spherical surface through its side to a depth sufficient to create an aperture in the form of a curvilinear slot 103 in the conduit wall. Again, the ends of the slot are located to coincide with the outer portions of the circumferences of the holes 32b and 34b through the tip insert 99. In this instance, the inside of the closed end 19b of the housing 17b is also formed of a spherical surface 104. The interior side walls of the bore formed in the housing to receive the valve body 21b, however, are straight to the point of intersection with the spherical face 104. There is no tapered inner portion of the housing such as the portion 23 of the device 13 (FIG. 2). Thus, a circumferential surface 105 of the tip insert 99 is straight and formed at right angles with the top surface 33b of the tip insert rather than being tapered inwardly as the circumferential surface 35 (FIG. 3). As may be seen in FIG. 11, the liquid and bacterial seal is formed between the spherically shaped interfacial portions of the outer perimeter of the bottom face 101 and the matching spherical surfaces of the inside bottom face 104 of the housing and the walls of the conduit 15b.

As mentioned previously, because the blood access device is inserted within a living body, it is important that the material of the device be biocompatible (biologically compatible) with the blood and living tissues which surround it. Furthermore, the device, once inserted, should not prevent healing, irritate tissues, or stimulate a strong or prolonged rejection response by the living body, and the material of the device should be physiologically inert over long periods of time in addition to being mechanically strong and reliable.

In accordance with the invention, a coating of carbon is utilized on all blood contacting surfaces and on the housing/skin interface. This carbon coating may be pyrolytic carbon, vapor-deposited carbon or vitreous carbon, and these kinds of coatings may be utilized on different parts of the blood access device 13. Pyrolytic carbon, vitreous (glassy) carbon and vapor-deposited carbon are compatible with the surrounding tissues over prolonged time periods when inserted through the skin layer of a living body. Preferably, pyrolytic carbon and/or vapor-deposited carbon are used. These coatings do not tend to irritate the surrounding skin tissues and promote the establishment of a barrier to external pathogens.

In general, the preferred construction of the device 13 includes a metallic housing, such as titanium, stainless steel or a chromium-cobalt alloy such as VITALLIUM. Preferably, the housing is constructed of titanium. The conduit 15 is constructed of pyrolytic carbon and may be formed in any suitable manner, such as deposition of a built-up coating on a mandrel, after which the mandrel is removed, leaving the tubelike structure. The valve body 21 is constructed also preferably of metal, such as titanium.

The metallic construction of both the housing and the valve body lends itself to machinability in the forming of these respective parts. The general bore in the housing which receives the valve body 21 is easily formed as are the threads on the outer portion of the housing wall to receive the cap 43. The two bores 24 and 39 (FIG. 2) in the valve body 21 also are readily formed by machining, as are the two longitudinal passages 45 and 47.

The tip insert 25 is constructed by preshaping a suitable substrate, such as a graphite core, in the general shape shown in FIG. 3. The holes 32 and 34 are then provided in the core, as by drilling. The coating of the pyrolytic carbon is then made thereon, including the inner surfaces of the holes 32 and 34, to provide the layer 27. The interfacial surfaces, particularly the tapered circumferential surface 35 and the bottom face 37, are lapped and polished to enhance a close-fit relation with adjacent parts. The tapered inner portion 23 of the housing is also lapped and polished. The button 77 is also constructed on a suitable substrate or graphite core which is preshaped to the desired form and includes both the smaller flange 79 and the larger flange 81, the holes 83 then being formed in the flange 81, such as by drilling, and a pyrolytic carbon coating being applied to the core, including the inner surfaces of the holes 83. Preferably, the carbon coating on this button has a rough finish. The core materials and the process of applying the pyrolytic carbon coatings are described in detail hereinafter. The cap 43 is made preferably of a machinable metal, such as stainless steel.

One such blood access device 13 has been constructed in which the overall length of the housing 17 is approximately 0.8 inch and its outer diameter is approximately 0.35 inch. The overall diameter of the large flange 81 is approximately 0.75 inch and the overall diameter of the flexible flange 87 (FIG. 7) is approximately 1.5 inches. The holes 83 in the flange 81 and the holes 89 in the flexible flange 87 are 0.1 inch in diameter. The pyrolytic carbon wall thickness of the conduit 15 is approximately .020 inch.

These dimensions are provided by way of giving an example of construction, and there is no intention of requiring the construction to be limited to any of these dimensions.

Referring now to FIGS. 2, 5, 9, and 11, a very important step in making the blood access device is the lapping of the portions of the body walls of the conduit 15 and the surfaces of the tip insert 25 to conform all of these portions in a close-fitting relation to one another. Such provides a good seat for the valve 21 and seal for the entire device 13.

In operation, after the valve 21 is closed, any residual blood in the valve body may be flushed out by using a suitable cleansing solution. Thereafter, a suitable cover (not shown) may be applied over the end of the cap 43 to keep the interior clean until the next use.

The pyrolytic carbon may be deposited upon the mandrels in the instance of the conduits 15 and 17 and upon the core materials for the other parts in the manner described in U.S. Pat. No. 3,783,868 and U.S. Pat. No. 3,298,921. An example of a coating method that may be employed is that of supporting the formed substrate on a rotating or stationary mandrel within a large fluidized bed, as discussed in the aforementioned patents, or coating on freely moving rods in a fluid bed.

Pyrolytic carbon is, by definition, deposited by the pyrolysis of a carbon-containing substance. Accordingly, the core material on which the pyrolytic carbon is deposited will be subject to the fairly high temperatures necessary for pyrolysis. Generally, hydrocarbons are employed as the carbon-containing substance to be pyrolyzed, and temperatures of at least about 1000° C are used. Some examples of deposition of pyrolytic carbon are set forth in the aforementioned U.S. Pat. No. 3,298,921. Processes illustrated and described in this patent employ methane as the source of carbon and utilize temperatures generally in the range of about 1200° C to 2300° C. Although it is possible to deposit pyrolytic carbon having the desired properties with regard to this invention at somewhat lower temperatures by using other hydrocarbons, for example, propane or butane, it is generally considered that the core material should remain substantially stable at temperatures of at least about 1000° C and preferably at even higher temperatures. Pyrolytic carbons deposited at temperatures below about 1500° C are particularly suited for use in the blood access device 13, because such pyrolytic carbons have exceptional tissue compatibility and mechanical reliability.

Examples of core materials which have the aforementioned stability at high temperatures include artificial graphite, boron carbide, silicon carbide, refractory metals (and alloys), such as tantalum, titanium, molybdenum, tungsten, and various ceramics, such as mullite. A preferred substrate material is polycrystalline graphite. An example of such a graphite is the polycrystalline graphite sold under the trademark POCO.

Vapor-deposited carbon coatings may be applied by the process described in U.S. Pat. No. 3,952,334 "Biocompatible Carbon Prosthetic Devices", issued Apr. 27, 1976. As generally described therein, a substrate is placed in an evaporative coater and a vacuum is established. A crucible within the coater, filled with a commercial grade of artificial graphite, is heated by electron beam bombardment. Coating is carried out until the desired thickness of carbon is deposited and the substrate is then removed. This process results in an exterior carbon layer that is smooth and uniform.

Summarizing, there has been described a device for providing access to the circulatory system of a living body for simultaneous withdrawal from and return of blood to the system. The deivce includes a tubular conduit of generally circular cross section which is insertable in a living blood vessel and a generally cylindrical housing having one of its ends closed and extending transversely of and adjoining this conduit at the closed end of the housing. The point of adjoining is centered with respect to the closed end of the housing so that the axes of the conduit and the housing form a right angle and intersect one another. The wall of the conduit intersects the housing at this point of adjoining. The housing has fluid communication with this conduit through an aperture in the conduit wall at the point of intersection, and the housing has a length sufficient to extend from the blood vessel to a point outside the living body in which it is implanted. A valve body is provided in the housing. The valve body has a pair of spaced apart longitudinal passages located to be alignable with the aperture at a given rotative position of the valve body in the housing. The valve body is adapted to receive a catheter tip in each of its longitudinal passages and in fluid communication with these passages. The valve body is coaxially rotatable in the housing between positions of alignment and nonalignment of these passages with the aperture to selectively establish fluid communication between the circulatory system and the catheters when they are inserted in the valve body. The device also includes means for forming a seal around the aperture between the valve body and the conduit at all times, i.e., whether the valve is open or closed.

While the invention has been described in connection with a preferred embodiment and certain alternatives thereof, modifications, variations, and other alternatives may be apparent to those skilled in the art in view of the foregoing description. Accordingly, it is intended to embrace all such alternatives, modifications, and variations as fall within the spirit and scope of the appended claims.

What is claimed is:

1. A device to provide access to the circulatory system of a living body for simultaneous withdrawal from and return of blood to the system comprising a tubular conduit of generally circular cross section insertable in a living blood vessel; a generally cylindrical housing having one closed end and extending transversely of and adjoining said conduit at the closed end, the point of adjoining being centered with respect to the closed end of said housing such that the axes of the conduit and the housing form a right angle between them and intersect one another, the wall of said conduit intersecting said housing at said point of adjoining and said housing having a length sufficient to extend from the blood vessel to a point outside the living body; an aperture in the conduit wall at the point of intersection of said conduit with said housing to provide fluid communication between the two; a valve body in said housing, said valve body having therethrough a pair of spaced apart longitudinal passages located to be alignable with said aperture at a given rotative position of said valve body, said valve body being adapted to receive a catheter tip in each of said longitudinal passages and in fluid communication therewith, and said valve body being coaxially rotatable in said housing between positions of alignment and nonalignment of said passages and said aperture to selectively establish fluid communication between the circulatory system and the catheters when inserted in said valve body; and means for forming a seal around said aperture, the seal being maintained in all rotative positions of said valve body.

2. A device in accordance with claim 1 wherein said seal means comprises a tip insert affixed in a bore in the inner end of said valve body and having a side circumferential surface substantially equal to the diameter of said valve body and adjoining the outer surface of said valve body at its inner end but tapering inwardly therefrom to a flat bottom surface having a diameter less than the diameter of said valve body and wherein said housing has an inner tapering portion closely conforming to said tapering circumferential surface and located to oppose said tapering circumferential surface when said valve body is in position in said housing, a seal being effected at the interface of these two tapering surfaces, and further comprising compression means holding the valve body in a seated relation within said housing at all rotative positions of said valve body and during rotation.

3. A device in accordance with claim 2 wherein said aperture in said conduit wall is in the form of a slot resulting when a plane parallel to the conduit axis is passed through the conduit wall at a depth sufficient to exceed the thickness of the wall and define a slot exposed thereby having a width substantially equal to the diameter of said longitudinal passages and a length substantially equal to the diameter of the flat bottom face of said insert, a seal also being effected at the interfacial surfaces between the flat bottom face and the opposing exposed portions of the wall of the conduit cut by the plane on either side of the aperture.

4. A device in accordance with claim 3 wherein the surfaces of said insert and said conduit are pyrolytic carbon.

5. A device in accordance with claim 2 wherein said compression means comprises a counterbore in the open end of said valve body, a coil spring in said counterbore, and a cap over the open ends of said housing and valve body, said cap being of the screw type and having an inner surface bearing against the spring to provide compression for retaining the valve body in a seated condition in the housing.

6. A device in accordance with claim 1 further comprising an interlock system between said device and the catheter tips inserted for fluid communication in said valve body.

7. A device in accordance with claim 6 in which said interlocking system includes a cap over the open end of said housing and valve body, said cap being of the screw type and having a pair of orifices spaced apart 180° from each other along a diameter of the cap and a pair of opposing curvilinear slots extending from a portion of the circumference of each of the orifices in the same direction therefrom around the periphery of the cap, the curvilinear slots having a width substantially less than the diameter of the orifices and a length of approximately one-quarter of a circle, said cap further including an inner slot within its body in the walls of each said curvilinear slot, and a lug on each of said catheter tips, said lug extending outwardly at right angles from said cathether tip walls, said lug being flat in end view and having a dimension in plan view substantially equal to said orifices and said inner slots, whereby the catheters after being inserted in said valve body may be utilized for rotating said valve body between the positions of alignment and nonalignment of the passages and the aperture and said lugs in said inner slot secure in the position of the catheters after rotation of the valve body to prevent inadvertent removal of the catheters when the parts are aligned.

8. A device in accordance with claim 2 wherein said aperture in said conduit wall is in the form of a slot made in a flat surface of a portion of the conduit wall resulting when a plane parallel to the conduit axis is passed through the conduit wall at a depth less than the thickness of the wall, the slot being formed of a width substantially equal to the diameter of said longitudinal passages but less than the width of the flat portion of the conduit wall and a length less than the diameter of the flat bottom face of said insert, a seal also being effected at the interfacial surfaces between the flat bottom face and flat portions of the conduit wall completely surrounding said slot.

9. A device in accordance with claim 1 wherein said seal means comprises a tip insert affixed in a bore in the inner end of said valve body and having a side circumferential surface substantially equal to the diameter of said valve body and adjoining the outer surface of said valve body at its inner end and effectively extending its length, the bottom face of said insert being spherically shaped, and wherein said housing has an inner bottom surface of spherical shape closely conforming to the bottom face of said insert and opposing same when said valve body is in position in said housing, a seal being effected at the interface of these two spherical surfaces, and further comprising compression means holding the valve body in a seated relation within said housing at all rotative positions of said valve body and during rotation.

* * * * *